United States Patent [19]
Gargano et al.

[11] 4,326,059
[45] Apr. 20, 1982

[54] PROCESS FOR THE PRODUCTION OF THIOPHOSPHORIC ACID ESTERS

[75] Inventors: Robert Gargano; Donald E. Perez; David K. Williams, all of Mobile, Ala.

[73] Assignee: Ciba-Geigy Corporation, Ardsley, N.Y.

[21] Appl. No.: 161,475

[22] Filed: Jun. 20, 1980

Related U.S. Application Data

[63] Continuation of Ser. No. 16,753, Mar. 2, 1979, abandoned, which is a continuation of Ser. No. 865,098, Dec. 27, 1977, abandoned.

[51] Int. Cl.$^3$ ............................................... C07F 9/65
[52] U.S. Cl. ................................................... 544/243
[58] Field of Search ........................... 544/243; 16/753

[56] References Cited
U.S. PATENT DOCUMENTS 3,657,247  4/1972  Freeman et al. .................... 544/243
4,007,197  2/1977  Freedman et al. ............. 544/243 X
4,012,506  3/1977  Balke et al. ...................... 544/243 X Primary Examiner—Donald G. Daus
Assistant Examiner—Diana G. Rivers
Attorney, Agent, or Firm—Karl F. Jorda

[57] ABSTRACT

An improved process for the production of dialkoxy phosphoric acid esters of substituted hydroxypyrimidines which involves reacting a dialkyl phosphoric acid halide with a substituted hydroxypyrimidine reaction in a two-step reaction is disclosed. In reaction step (a) the hydroxypyrimidine derivative is converted with the aid of sodium hydroxide and in the presence of a hydrocarbon solvent and a phase-transfer catalyst to the sodium salt while drying the reaction mixture by azeotropically removing water. In step (b) the condensation process is carried out at room temperature to about 100° C. The condensation step may be accelerated by addition of 4-bis($C_1$ to $C_4$ alkyl)aminopyridine as catalyst.

11 Claims, No Drawings

PROCESS FOR THE PRODUCTION OF THIOPHOSPHORIC ACID ESTERS

CROSS-REFERENCE TO RELATED APPLICATIONS

This is a continuation of application Ser. No. 16,753, filed on Mar. 2, 1979, now abandoned, which is a continuation of application Ser. No. 865,098, filed Dec. 27, 1977, now abandoned.

DETAILED DISCLOSURE

This invention relates to an improved process for preparing esters of thiophosphoric acid and, more specifically, thiophosphoric acid esters of substituted hydroxypyrimidines.

More particularly, the present invention pertains to the manufacture of esters of dialkoxy thiophosphoric acids of the following general formula:

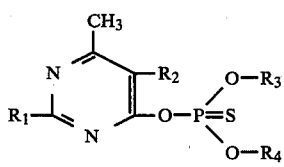

wherein $R_1$ represents lower alkyl, lower alkenyl, lower alkoxy(lower)alkyl or lower alkylmercapto(lower)alkyl, $R_2$ stands for hydrogen, lower alkyl or lower alkenyl and $R_3$ and $R_4$ are lower alkyl.

These compounds which are disclosed and claimed in U.S. Pat. No. 2,754,243, and especially O,O-diethyl-O-(2-isopropyl-4-methyl-6-pyrimidyl)thiophosphate (Diazinon ®), are of great commercial value by virtue of their well-established insecticidal and acaridical activity and consequent usefulness in pest control.

According to prior art practices, the compounds of the above formula were initially produced by reacting an aliphatic thiophosphoric acid diester halide of the formula:

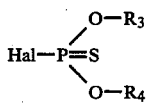

wherein Hal represents chlorine or bromine and $R_3$ and $R_4$ are as defined hereinabove, with a hydroxypyrimidine of the formula:

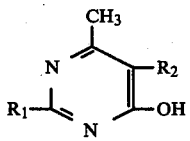

wherein $R_1$ and $R_2$ have the significance given to them above, in the presence of benzene as solvent and an alkali metal carbonate as acid binding agent.

However, the practice of such a process entailed certain drawbacks and disadvantages with respect to duration of the reaction as well as yield and purity of the final product.

It was then found that dialkoxy thiophosphates of Formula I could be advantageously produced in a considerable shortened period of time by means of a procedure which utilized various catalysts, as for instance, mercury salts, e.g. mercury chlorides and iodides (U.S. Pat. No. 3,107,245) and copper salts, e.g. cupric chloride and cupric nitrate (U.S. Pat. Nos. 3,107,246 and 3,367,935), especially when added to the reaction mixture during the course of refluxing as small aliquots of a solution of the catalyst (U.S. Pat. No. 3,329,678).

However, while these catalytic processes constituted advancements and improvements in the production of the subject dialkoxy thiophosphates, other problems and disadvantages surfaced. It was found that in these processes, e.g., in the conventional and commercial sodium carbonate/copper chloride process, significant amounts of impurities were frequently produced which increased the cholinesterase activity of these phosphoric acid esters. The presence of a catalyst of this type contributes to the formation of cholinesterase-inhibiting impurities by catalyzing side reactions. These impurities are in the production of Diazinon, for example, S-TEPP (monothionotetraethylpyrophosphate), SS-TEPP (dithionotetraethylpyrophosphate), the oxo-derivative (which has oxygen in lieu of the sulfur atom) and others the exact nature of which is not known. These impurities are formed in amounts of 0.5% or greater. Significant amounts of such cholinesterase-inhibiting impurities are also formed after manufacture due to decomposition of these phosphoric acid esters.

Cholinesterase inhibition means inhibition of the enzymatic activity of cholinesterase, i.e., interference with the hydrolysis of acetylcholine which allows the accumulation of sufficiently large amounts of acetylcholine to affect nerve activity and corresponding muscular control adversely. [Wayland J. Hays, Chemical Handbook on Economic Poisons, U.S. Dept. of Health, Education and Welfare, p. 12 (1963)]. An increase of the cholinesterase activity of the subject phosphoric acid esters due to cholinesterase-inhibiting impurities is undesirable from the point of view of operators who handle these phosphoric acid esters or warm blooded animals that may come into contact therewith. Accordingly, when in the past a batch of phosphoric acid esters either by formation during manufacture or by decomposition after manufacture contained those undesirable cholinesterase-inhibiting impurities to the extent of less than 1 gamma, the batch could not be utilized commercially.

In commercial practice cholinesterase-inhibiting impurities had to be removed in a separate subsequent processing step involving the refluxing of the reaction product in an inert organic solvent with a basic material such as sodium hydroxide, as disclosed and claimed in U.S. Pat. No. 3,432,503, or a catalyst-free process with an elevated temperature, a non-polar solvent, sodium or potassium hydroxide as acid acceptor and careful control of the mode of addition of the reactants as disclosed and claimed in U.S. Pat. No. 4,066,642, had to be resorted to.

It is the principal object of this invention to produce dialkoxy thiophosphates of formula I of excellent quality and color and in excellent yield.

It is a further important object of this invention to minimize and reduce the formation of the undesirable cholinesterate-inhibiting impurities during the reaction so that the desired product contains at most only trace amounts and so that no separate removal or other special operation is necessary.

It is yet another object of this invention to reduce the reaction time of the process and to carry out the condensation step at a low temperature range for experience has shown that conducting the condensation reaction at temperatures greater than 105° C. may cause quality problems and running it at temperatures of about 130° C. may cause detonation of the ester halides of formula II.

The above-mentioned objectives can be accomplished by the subject inventive process which comprises condensing a thiophosphoric acid diester halide of formula II and a hydroxypyrimidine of formula III in a two-step process separating the condensation step (b) from an introductory step (a) which comprises the conversion of the hydroxy-pyrimidine derivative to the more reactive ionic sodium salt while at the same time removing the water present by an azeotropic distillation with the aid of an appropriate hydrocarbon solvent. The thus-dried slurried reaction mass is then subjected to reaction with the thiophosphoric acid diester halide of formula II at low temperature. Though strictly separated from each other both steps (a) and (b) are part of one process sequence.

The process of this invention is further improved by the addition of a phase transfer catalyst in the dehydration step (a).

This process is the first synthesis in this chemical area that separates the condensation reaction from the reaction mass dehydration. This is a significant improvement because:

(a) The absence of water during the condensation reaction results in the formation of lower amounts of impurities.
(b) The absence of water allows the condensation reaction to be performed at lower temperatures which also results in the formation of lower amounts of impurities and improved product color.
(c) A wide range of high boiling solvents can be used for water removal, which results in a faster drying time without being limited by the detonation point of the ester chlorides at a temperature of about 130° C.

In other words, step (a) results in a reaction mass exhibiting optimal reaction conditions for the condensation reaction (b) at a low temperature of about room temperature to about 100° C., preferably 60° to 80° C.

Step (a) comprises converting the oxypyrimidine derivative into the far more reactive ionic form by treating it with a sodium hydroxide solution of 70% to 40% whereby additional water is produced according to the following equation:

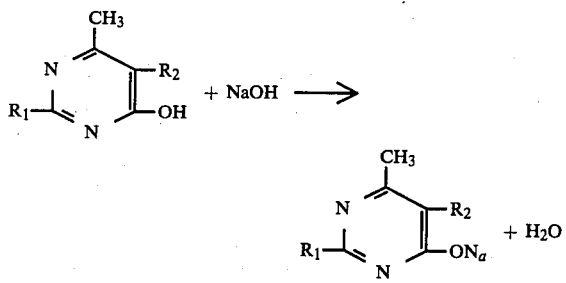

A 70 to 50% sodium hydroxide solution is preferred. However, the water present in the reaction by way of the aqueous sodium hydroxide solution has to be removed before the condensation step (b) starts because of its hydrolytic decomposition effect on the reactants.

Removal of water may very easily be carried out at an elevated temperature by hydrocarbon solvents capable of forming azeotropic mixtures with water which have a lower boiling point than the solvent itself. Under refluxing conditions, water will be continuously removed. However, the time of reaction will be prolonged when excessive amounts of water are present as a result of using diluted solutions of sodium hydroxide, e.g., 30% or less.

From the above reaction conditions it is clear that during most of the reaction time a two-phase system exists comprising among others water-insoluble hydrocarbon solvent and water.

It has been found and is a preferred embodiment of the inventive process that especially aromatic hydrocarbons having a boiling point below 150° C. possess the desired properties dissolving hydroxypyrimidine derivatives of formula III and of forming azeotropic mixtures with water sufficiently effective to remove reasonable amounts of water.

Preferred solvents are aromatic hydrocarbons, such as, for example, benzene, toluene, xylene, mesitylene, ethylbenzene, cumene, etc. Especially preferred is toluene but most preferred, however, is xylene because it forms a xylene-water azeotrope which contains twice the weight faction of water than the toluene-water azeotrope, namely 40% of water. Moreover, xylene is capable of dissolving most of the hydroxypyrimidine of formula III. Thus, for example, 2-isopropyl-4-methyl-6-hydroxypyrimidine will be dissolved completely under usual reaction conditions.

The two-phase system of the dehydration step (a) advantageously comprises an effective amount of a phase transfer catalyst of about 0.5 to about 3 mole % in relation to the amount of the reactant of formula II. Said catalyst is a quaternary ammonium salt of the formula $N(R_7, R_8, R_9, R_{10})\oplus Y\ominus$, wherein $R_7$ to $R_{10}$ independently represent an alkyl, aryl, aralkyl, cycloalkyl or alkaryl group, each having at most 12 carbon atoms, while Y is a neutralizing anion, advantageously selected from common inorganic salts, such as chlorides, bromides, iodides, sulfates, hydrogen sulfates, phosphates, perchlorates, nitrates and others. However, it has been found that for the purposes of this invention, the tetra ($C_1$ to $C_4$ alkyl) ammonium salts are particularly useful. The alkyl groups therein may be equal or different. The anion in such salts may be derived from inorganic acids, such as, hydrochloric acid, hydrobromic acid and sulfuric acid. Preferred embodiments among these catalysts are tetra-($C_1$ to $C_4$ alkyl)ammonium-halide or -hydrogensulfate, such as, the chlorides and hydrogen sulfates as, for example, tributylmethylammonium chloride or tetrabutylammonium hydrogen sulfate.

The dehydration of the reaction mass is simply controlled by the temperature in the refluxing device. A rising of the lower boiling point of the azeotrope to the boiling point of the pure hydrocarbon solvent will indicate removal of the water and completion of the salt formation. At this time the reaction mass will consist of a milky or sticky slurry sodium salt of the hydroxypyrimidine of formula III in the hydrocarbon solvent.

The reaction mass thus obtained is then subjected to reaction with the halothiophosphate derivative of formula II. The temperature should range between room temperature to 100° C., with the range of 60° to 80° C., however, being preferred. The temperature range may additionally be lowered to 40° to 60° C. (within a possible range of 30° to 100° C.) when the reaction step (b) is carried out in the presence of 4-[bis($C_1$-$C_4$alkyl)-]aminopyridine, which is preferably used in catalytic amounts of 0.01 to 1.0 mole % of the amount of halothiophosphate derivative of formula II present. The most preferred catalytic amount of 4-bis(alkyl)aminopyridine is 0.02 to 0.05 mole-%. The preferred catalyst for the condensation step (b) is 4-dimethylaminopyridine.

As with all reactions involving a phase transfer catalyst agitation of the reaction mass is important. Poor agitation results in longer reaction times.

In summary, the invention is directed to an improved process for preparing a thiophosphoric acid ester of the formula II with an hydroxypyrimidine derivative of the formula III the improvement being a two-step process which comprises (a) in a first step, converting the reactant of formula III into the sodium salt with the aid of sodium hydroxide solution consisting of 70 to 40% sodium hydroxide under reflux in a hydrocarbon solvent capable of removing water by azeotropic distillation below the decomposition point of the hydroxypyrimidine of formula III and in the presence of about 0.5 to about 3 mole-% of a quaternary ammonium salt of the formula $N(R_7, R_8, R_9, R_{10})^+ Y^-$ as a phase transfer catalyst, wherein $R_7$ to $R_{10}$ independently represent an alkyl, aryl, aralkyl, cycloalkyl or alkaryl group, each with at most 12 carbon atoms and Y is a neutralizing anion, and continuously removing water by an azeotropic distillation, and (b) in a second condensation step, adding to the thus dried slurried reaction mass at a temperature from about room temperature to about 100° C. the reactant of formula II. An amount of a 4-bis(alkyl)aminopyridine may be a helpful additive to accelerate the reaction.

The invention is illustrated but not limited by the following Examples.

EXAMPLE 1

Two-Step Reaction with Catalyst in the First Step

To a 2 liter baffled 5 neck flask equipped with thermometer, stirrer, condenser and coalescer the following reactants were charged:

300.0 grams xylene (b.p. 137°–141° C.)
159.8 grams 100% isopropyl-4-methyl-6-hydroxypyrimidine (5 mole % excess)
83.2 grams 50% NaOH (4 mole% excess)
4.67 grams 75% tributyl methyl ammonium chloride (1.5 mole%)

Agitation was applied. The reaction mass was then heated to reflux. Water was removed from the distillate while returning the organic phase to the reactor until the reaction mass becomes dry. Initially the boiling point of the reaction mass was below that for xylene since xylene-water forms a minimum boiling point azeotrope. When the reaction mass was dry, the boiling point became that of the pure component.

The dried reaction mass was cooled to 70° C. and 188.6 grams, 100% O,O-diethyl thiophosphoric acid chloride (ester chloride) was charged. The temperature was maintained at 70° C. for 4 hours. (During the first hour, the reaction mass was cooled, while during the second through fourth hours the reaction mass was heated to maintain 70° C.).

After four hours the reaction mass was washed as follows: 200.0 grams water and 20.0 grams of 93% $H_2SO_4$ was charged. The mixture was then agitated 5 minutes. The bottom aqueous phase was decanted. Then 100.0 grams water and 30.0 grams 50% NaOH were charged. The mixture was then agitated for 5 minutes and the bottom aqueous phase was decanted. The organic phase was quantitatively transferred to a tared 2 liter, round bottom boiling flask. The solvent was removed from the product by vacuum distillation at 110° C. and 10 mm Hg absolute pressure to obtain 298 g of 96.3% Diazinon (yield 94.5% of theory).

EXAMPLE 2

Two-Step Reaction with Catalyst in Each Step

The same procedure given in example #1 was followed except, that after the reaction mass was dried, its temperature was lowered to 50° C. and 0.037 grams of 100% 4-dimethylaminopyridine (0.03 mole %) was added with the O,O-diethyl thiophosphoric acid chloride. The reaction mass was then agitated for 3 hours at 50° C. The product was then isolated as described in Example 1 to obtain 299.6 grams of 97.1% Diazinon (yield 96.0% of theory).

EXAMPLE 3

Typical Results from Reactions Described in Examples 1 and 2

| Batch I.D. | Mole % Catalyst TBMAC[1] | Mole % Catalyst 4-DMAP[2] | Solvent | Reaction Temp. °C. | Yield % | Assay % |
|---|---|---|---|---|---|---|
| 1303-16 | 1.5 | .36 | Xylene | 50 | 93.9 | 94.4 |
| 1303-20 | 1.5 | .02 | Xylene | 50 | 95.4 | 95.4 |
| 1303-26 | 1.5 | .03 | Toluene | 50 | 95.0 | 96.7 |
| 1303-6 | 1.5 | 0 | Xylene | 70 | 94.5 | 96.3 |
| 1303-1 | 1.5 | 0 | Xylene | 100 | 90.5 | 93.6 |
| 1303-18 | 3.0 | 0 | Xylene | 70 | 93.2 | 93.5 |
| P.P.-18 | 1.5 | 0 | Toluene | 75 | 96.0 | 97.1 |

[1]Tributylmethyl ammonium chloride
[2]4-Dimethyl amino pyridine

EXAMPLE 4

Influence of Agitation on Reaction Time

Four experiments were performed in a standard baffled 2 liter reaction flask using identical reaction conditions except for the size of the agitator blade. The following results were obtained.

| Agitator Blade Size | Reaction Time Hours | Residual Ester Chloride Level |
|---|---|---|
| 5 cm × 2 cm | 7 | 1.0% |
| 5 cm × 2 cm | 4 | 2.0% |
| 7½ cm × 2 cm | 4 | 0.25% |
| 11 cm × 2.5 cm | 2 | 0.25% |

What is claimed is:

1. In a process for the production of thiophosphoric acid esters of the formula I

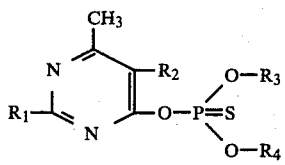

wherein $R_1$ is lower alkyl, lower alkenyl, lower alkoxy(lower) alkyl or lower alkylmercapto(lower)alkyl, $R_2$ is hydrogen, lower alkyl or lower alkenyl and $R_3$ and $R_4$ are lower alkyl, which comprises reacting a dialkyl phosphoric acid halide of formula II

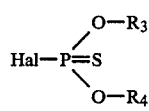

wherein Hal represents chlorine or bromine and $R_3$ and $R_4$ are as defined hereinabove with a hydroxypyrimidine of the formula III

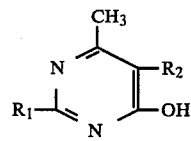

wherein $R_1$ and $R_2$ have the significance given to them above, in the presence of an organic solvent, the improvement which comprises (a) in a first step, converting the hydroxypyrimidine reactant of formula III into the sodium salt with the aid of a sodium hydroxide solution consisting of 70% to 40% sodium hydroxide under reflux in an aromatic hydrocarbon solvent capable of removing water by azeotropic distillation below the decomposition point of the hydroxypyrimidine of formula III and in the presence of about 0.5 to about 3 mole-% of a quaternary ammonium salt of the formula $N(R_7, R_8, R_9, R_{10})\oplus Y\ominus$ as a phase transfer catalyst wherein $R_7$ to $R_{10}$ independently represent an alkyl, aryl, aralkyl, cycloalkyl or alkaryl group each with at most 12 carbon atoms and Y is a neutralizing anion selected from among chlorides, bromides, iodides, sulfates, hydrogen sulfates, phosphates, perchlorates, nitrates and continuously removing water by an azeotropic distillation, (b) in a second, condensation step, adding to the thus-dried slurried reaction mass at a temperature of about 60° to 80° C. the reactant of formula II.

2. A process according to claim 1, wherein in the first step a 70% to 50% sodium hydroxide solution is used.

3. A process according to claim 1, wherein the solvent used is an aromatic hydrocarbon solvent boiling below 150° C.

4. A process according to claim 3, wherein the solvent used is xylene.

5. A process according to claim 1, wherein $R_7$, $R_8$, $R_9$, and $R_{10}$ in the quaternary ammonium salt of the formula $N(R_7, R_8, R_9,$ and $R_{10})\oplus Y\ominus$ represent different or equal $C_1$ to $C_4$ alkyl groups.

6. A process according to claim 1, wherein as phase transfer catalyst tributylmethylammoniumchloride or tetrabutylammoniumhydrogensulfate is used.

7. A process according to claim 1, wherein the condensation step (b) is carried out in the presence of 4-[bis($C_1$-$C_4$ alkyl)]aminopyridine at about room temperature to about 100° C.

8. A process according to claim 7, wherein 4-[bis($C_1$-$C_4$alkyl)]aminopyridine is used in catalytic amounts of 0.01 to 1.0 mole-% of the amount of reactant of formula II.

9. A process according to claim 8, wherein the catalyst is used in amounts of 0.02 to 0.03 mole-%.

10. A process according to claim 7 wherein 4-dimethylaminopyridine is used as catalyst.

11. A process according to claim 1 for preparing the compound of the formula

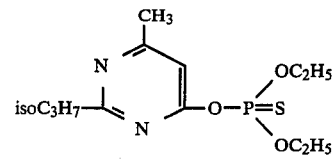

by condensing reactants IIa

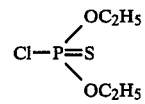

and IIIa

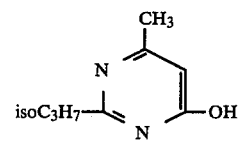

following reaction steps (a) and (b).

* * * * *

UNITED STATES PATENT AND TRADEMARK OFFICE
CERTIFICATE OF CORRECTION

PATENT NO. : 4,326,059
DATED : APRIL 20, 1982
INVENTOR(S) : ROBERT GARGANO, ET AL

It is certified that error appears in the above—identified patent and that said Letters Patent is hereby corrected as shown below:

Claim 9, Column 8, Line 27 reads:

"lyst is used in amounts of 0.02 to 0.03 mole-%"

Should read:

-- lyst is used in amounts of 0.02 to 0.05 mole-% --

Signed and Sealed this

Sixth Day of July 1982

[SEAL]

Attest:

Attesting Officer

GERALD J. MOSSINGHOFF
Commissioner of Patents and Trademarks